US00PP37745P2

(12) United States Plant Patent
Boxriker

(10) Patent No.: US PP37,745 P2
(45) Date of Patent: Oct. 6, 2026

(54) ***DAHLIA* PLANT NAMED 'KLEDH24735'**

(50) Latin Name: ***Dahlia* Sp.**
Varietal Denomination: KLEDH24735

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/341,868

(22) Filed: Sep. 26, 2025

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 5/02
See application file for complete search history.

(56) References Cited

PUBLICATIONS

Chrome-extension://efaidnbmnnnibpcajpcglclefindmkaj/https://www.log.no/wp-content/uploads/2024/08/G3-Ungplanter-nyhets-liste-2025_red.pdf; 2025; 3 pages.*
https://www.facebook.com/selectaone1/posts/may-we-introduce-our-dahlia-dalaya-meena-novelties-desna-surya-amal-kailua-indir/959951169467799/; May 25, 2024; 1 page.*
https://www.linkedin.com/posts/selecta-one_selectaone-welovetogrow-potplants-activity-7201160583788806144-t0eN; Printed Jan. 23, 2026 posted 1 year ago (Jan. 23, 2025); 1 page.*
chrome-extension://efaidnbmnnnibpcajpcglclefindmkaj/https://josvainiugeles.it/wp-content/uploads/2024/09/Selecta-Annuals-2025.pdf; 2025; 2 pages.*

* cited by examiner

*Primary Examiner* — Kent L Bell
(74) *Attorney, Agent, or Firm* — Weatherly IP Solutions, LLC; John E. Pritchard; James M. Weatherly

(57) ABSTRACT

A new *Dahlia* plant designated 'KLEDH24735' particularly distinguished by red flowers with white tips and a semi-upright plant habit, is disclosed.

1 Drawing Sheet

Genus and species: *Dahlia* sp.
Variety denomination: 'KLEDH24735'.

BACKGROUND

The present invention comprises a new and distinct variety of *Dahlia,* botanically known as *Dahlia* sp., and hereinafter referred to by the variety name 'KLEDH24735'. 'KLEDH24735' originated from an open pollination in a field with the proprietary female 'KLEDH20121' (U.S. Plant Pat. No. 33,926) and an unknown male *Dahlia* plant in the summer of 2020 in Latina, Italy. In March 2021, a seedling was selected and named 'KLEDH24735'. 'KLEDH24735' was first vegetatively propagated by vegetative cuttings in April 2021 in Latina, Italy. 'KLEDH24735' was found to reproduce true to type in successive generations of asexual propagation.

SUMMARY

The following are the most outstanding and distinguishing characteristics of 'KLEDH24735' when grown using standard horticultural practices in Latina, Italy.

1. Red ray florets with white tips; and
2. Semi-upright plant habit.

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph was taken during May 2024 in Stuttgart, Germany and shows the whole plant, including the inflorescences, foliage and buds.

The colors shown are as true as can be reasonably obtained by conventional photographic procedures.

DESCRIPTION OF 'KLEDH24735'

The following detailed descriptions set forth the distinctive characteristics of 'KLEDH24735'. The data which define these characteristics were collected from asexual reproductions carried out in Latina, Italy. Data was collected on 16-week-old plants, with one pinch and grown under natural light in a greenhouse. Color references are to The R.H.S. Colour Chart of The Royal Horticultural Society of London (R.H.S.), 5$^{th}$ edition (2007).

Classification:
*Family.*—Asteraceae.
*Botanical.*—*Dahlia* sp.
*Designation.*—'KLEDH24735'.

Parentage:
*Female parent.*—'KLEDH20121' (U.S. Plant Pat. No. 33,926).
*Male parent.*—Unknown male parent.

Propagation:
*Type.*—Vegetative terminal cuttings.
*Time to produce a rooted young plant.*—3 to 4 weeks.
*Time to produce a flowering plant.*—About 10 weeks.

*Root description*.—Color N155C, fine.
*Rooting habit*.—Freely branching and moderately dense.

Plant description:
*Plant and growth habit*.—Semi-upright.
*Plant height*.—To the top of foliar plane: About 18.0 cm. Including inflorescence: About 27.0 cm.
*Plant diameter*.—About 35 cm.

Lateral branches:
*Length*.—Up to the last pair of leaves: About 16 cm. Including inflorescence: About 27 cm.
*Diameter*.—About 0.4 cm.
*Internode length*.—From 3 cm to 6 cm.
*Strength*.—Medium strong.
*Texture*.—Smooth.
*Color*.—Close to 144A.

Foliage description:
*Arrangement*.—Opposite.
*Length*.—Up to 11.5 cm.
*Width*.—About 5 cm.
*Shape*.—Ovate.
*Apex*.—Broadly acuminate.
*Base*.—Acute.
*Margin*.—Serrate.
*Venation pattern*.—Pinnate.
*Venation color*.—146C.
*Texture*.—Upper and lower surface: Little hairy on the edges, slightly rugose and glossy.
*Color*.—Immature: Upper surface: N137A. Lower surface: 191A to 191B. Mature: Upper surface: N137D. Lower surface: 191A to 191B.

Petioles:
*Length*.—About 3.5 cm.
*Diameter*.—About 0.3 cm.
*Texture*.—Upper surface: Smooth. Lower surface: Smooth.
*Color*.—Upper surface: Close to 145A. Lower surface: Close to 146C.

Inflorescence description:
*Appearance and arrangement*.—Composite head inflorescence, daisy eyed, held above the foliage.
*Fragrance*.—None detected.
*Time to flower*.—About 10 weeks after potting.
*Post-production longevity*.—Plants flower continuously from spring through autumn.
*Typical and observed inflorescence lastingness*.—About 10 days, depending on the conditions.

Inflorescence bud:
*Height*.—About 1.2 cm.
*Diameter*.—About 1.4 cm.
*Shape*.—Globular.
*Color*.—144A at the base with 144D to 144C toward the tips.

Inflorescence size:
*Diameter*.—About 7 cm.
*Depth* (*height*).—About 4 cm.
*Disc diameter*.—About 0.8 cm.
*Receptacle height*.—0.3 cm.
*Receptacle diameter*.—About 1.3 cm.
*Receptacle color*.—143C.

Ray florets:
*Quantity per inflorescence*.—75 in 6 whorls.
*Length*.—3.2 cm.
*Width*.—About 1.5 cm.
*Shape*.—Oval.
*Apex*.—Pointed.
*Base*.—Fused in a tube.
*Margin*.—Entire.
*Aspect*.—Keeled.
*Texture*.—Upper surface: Smooth. Lower surface: Smooth.
*Color*.—Immature: Upper surface: 27C to 27D with 47A at marginal zone. Lower surface: 27D with 47A at marginal zone. Mature: Both surfaces: N155C with 47A at marginal zone of ray florets. The proportion of the two colors can change during the season and in different environmental conditions.

Disc florets:
*Quantity per inflorescence*.—37.
*Length*.—About 1 cm.
*Diameter*.—0.15 cm.
*Shape*.—Tubular.
*Texture*.—Inner surface: Smooth. Outer surface: Smooth.
*Color*.—Immature: Inner surface: 1B to 1C. Outer surface: 1B to 1C. Mature: Inner surface: 1C. Outer surface: 1C.

Phyllaries:
*Quantity per inflorescence*.—5 at the external whorl, 12 in the internal whorls.
*Length*.—External phyllaries about 1.1 cm; inner phyllaries about 1.6 cm.
*Width*.—External phyllaries about 0.5 cm; inner phyllaries about 0.7 cm.
*Shape*.—Lanceolate to spatulate.
*Apex*.—Broadly acute.
*Base*.—External phyllaries attenuate; fused the internal whorls.
*Margin*.—Entire.
*Texture*.—Upper surface: Smooth and slightly glossy. Lower surface: Smooth and slightly glossy.
*Color*.—Upper surface: external whorl: N137B. internal whorl: 143A at the base to 145D at the tips. Lower surface: external whorl: N137C. internal whorl: 143A at the base to 145C at the tips.

Peduncles:
*Length, terminal peduncle*.—Up to 14.0 cm.
*Length, axillary peduncle*.—Up to 9.0 cm.
*Diameter*.—About 0.2 cm.
*Strength*.—Medium strong.
*Texture*.—Smooth.
*Color*.—Close to 148A.

Reproductive organs:
*Androecium*.—Only on disc florets. Quantity per floret: 5 stamens with fused anthers. Filament length: 0.2 cm. Filament color: 149D. Anther shape: Oblong. Anther length: 0.25 cm. Anther color: 17A. Pollen amount: Average. Pollen color: 17A.
*Gynoecium*.—Present on ray and disc florets. Quantity per floret: 1. Pistil length: 0.65 cm. Style length: 0.3 cm. Style color: Close to 4D. Stigma shape: Bipartite. Stigma color: 1C. Ovary color: 149D.

Fruit and seed set: Not observed.

Disease and pest/insect resistance: No disease or pest/insect resistance observed.

COMPARISON OF 'KLEDH24735' WITH FEMALE PARENT AND KNOWN VARIETY

'KLEDH24735' is distinguished from the female parent as described in Table 1.

TABLE 1

| Comparison with Female Parent | | |
|---|---|---|
| Trait | Variety 'KLEDH24735' | Female parent 'KLEDH20121' |
| Flower color | Red ray florets with white tips | Red |

'KLEDH24735' can be compared to the commercial *Dahlia* variety 'KLEDH24716' (U.S. patent application Ser. No. 19/320,318). Differences between the varieties are described in Table 2.

TABLE 2

| Comparison with Similar Variety | | |
|---|---|---|
| Trait | Variety 'KLEDH24735' | Commercial line 'KLEDH24716' |
| Flower color | Red ray florets with white tips | Purple magenta with white tips |

I claim:

1. A new and distinct variety of *Dahlia* Plant Named 'KLEDH24735', as illustrated and described herein.

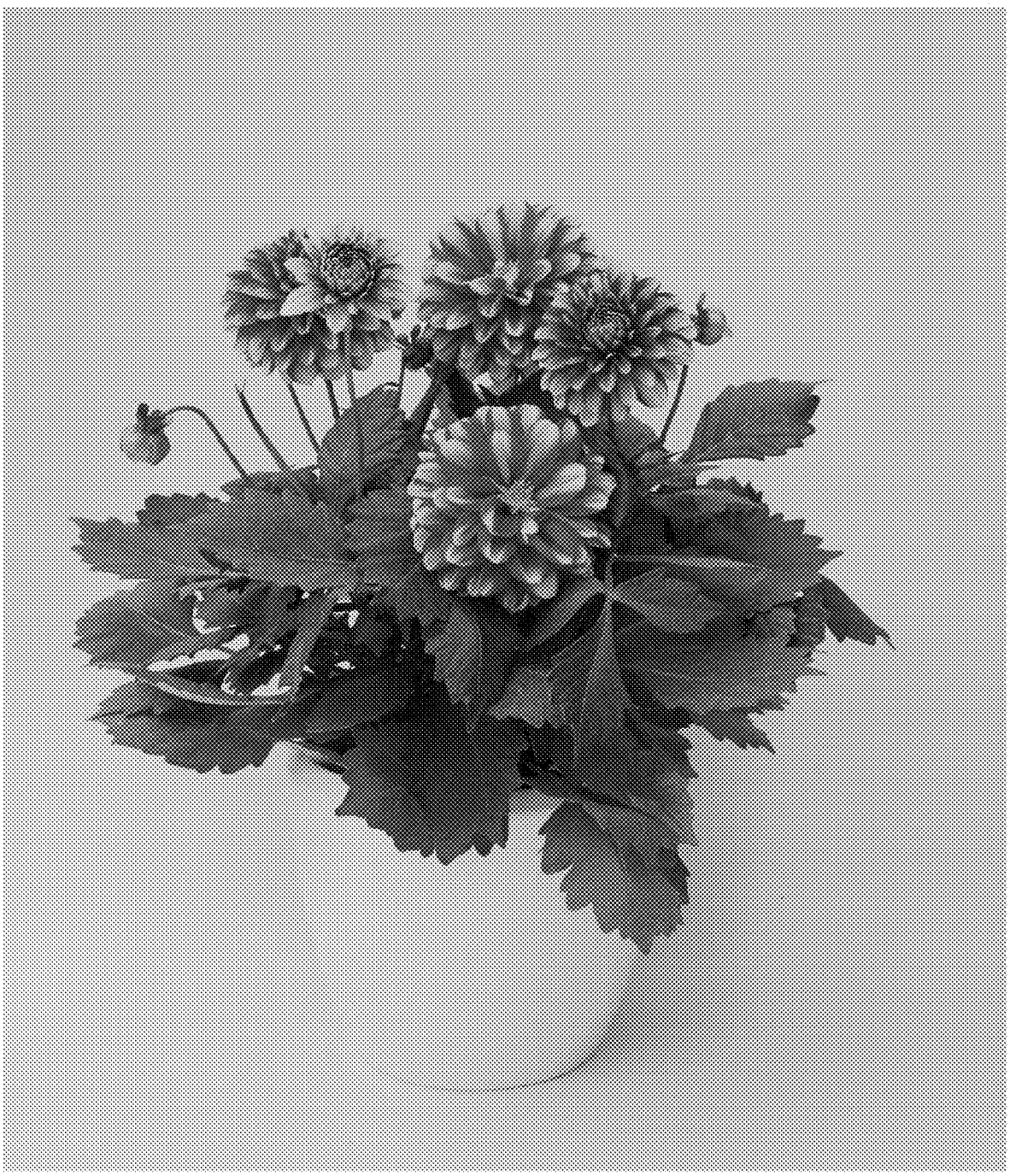

* * * * *